United States Patent
Jonnada et al.

(10) Patent No.: US 9,629,564 B2
(45) Date of Patent: Apr. 25, 2017

(54) ELECTROCARDIOGRAPH (ECG) SIGNAL PROCESSING

(71) Applicants: Sowmya Jonnada, Kakinada (IN); Venkat Natarajan, Bangalore (IN); Amit Baxi, Thane (IN)

(72) Inventors: Sowmya Jonnada, Kakinada (IN); Venkat Natarajan, Bangalore (IN); Amit Baxi, Thane (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/498,060

(22) Filed: Sep. 26, 2014

(65) Prior Publication Data

US 2016/0089047 A1 Mar. 31, 2016

(51) Int. Cl.
| | | |
|---|---|---|
| *A61B 5/04* | (2006.01) | |
| *A61B 5/0432* | (2006.01) | |
| *A61B 5/044* | (2006.01) | |
| *A61B 5/0456* | (2006.01) | |
| *A61B 5/0468* | (2006.01) | |

(Continued)

(52) U.S. Cl.
CPC ......... *A61B 5/04012* (2013.01); *A61B 5/044* (2013.01); *A61B 5/0432* (2013.01); *A61B 5/0452* (2013.01); *A61B 5/0456* (2013.01); *A61B 5/0468* (2013.01); *A61B 5/0472* (2013.01); *A61B 5/6801* (2013.01); *A61B 5/6802* (2013.01); *A61B 5/7203* (2013.01); *A61B 5/7239* (2013.01)

(58) Field of Classification Search
CPC ... A61B 5/7225; A61B 5/7207; A61B 5/7203; A61B 5/0402; A61B 5/04012; A61B 5/0432; A61B 5/044; A61B 5/0456; A61B 5/0468; A61B 5/0472; A61B 5/6801; A61B 5/6802; A61B 5/6804; A61B 5/681
USPC ........................................................ 600/516
See application file for complete search history.

(56) References Cited

U.S. PATENT DOCUMENTS

| | | |
|---|---|---|
| 4,769,760 A | 9/1988 | Kroll et al. |
| 2011/0040200 A1 | 2/2011 | Douglas et al. |

(Continued)

FOREIGN PATENT DOCUMENTS

| | | |
|---|---|---|
| TW | M427917 | 5/2012 |
| WO | WO 2010/077997 A2 | 7/2010 |

(Continued)

OTHER PUBLICATIONS

Eilers et al, "Baseline Correction with Asymmetric Least Squares Smoothing", Oct. 2005, 24 pages.

(Continued)

*Primary Examiner* — Paula J Stice
(74) *Attorney, Agent, or Firm* — David W. Osborne; Thorpe North & Western, LLP

(57) ABSTRACT

Technology for processing an electrocardiograph (ECG) signal is disclosed. The ECG signal can be identified, wherein the ECG signal is affected by baseline wander noise. Signal processing can be performed on the ECG signal affected by baseline wander noise in order to determine a start time and an end time for individual waveforms in the ECG signal affected by baseline wander noise. Features for the individual waveforms in the ECG signal can be extracted, wherein the features indicate one or more cardiac function metrics.

22 Claims, 11 Drawing Sheets

(51) Int. Cl.
   *A61B 5/0472*    (2006.01)
   *A61B 5/00*      (2006.01)
   *A61B 5/0452*    (2006.01)

(56) References Cited

U.S. PATENT DOCUMENTS

| | | |
|---|---|---|
| 2011/0184297 A1 | 7/2011 | Vitali et al. |
| 2012/0123232 A1* | 5/2012 | Najarian ............ A61B 5/0022 600/345 |
| 2013/0079655 A1 | 3/2013 | Hsu |
| 2014/0107507 A1* | 4/2014 | Ghosh ............... A61N 1/36507 600/509 |

FOREIGN PATENT DOCUMENTS

| | | |
|---|---|---|
| WO | WO 2012/104658 A2 | 8/2012 |
| WO | WO2014/052988 | 4/2014 |

OTHER PUBLICATIONS

Kaur et al, "Comparison of Different Approaches for Removal Baseline Wander from ECG Signal", ICWET, 2011, 7 pages, International Journal of Computer Applications.

Leski et al, "ECG baseline wander and powerline interference reduction using nonlinear filter bank", Signal Processing, 2005, pp. 781-793, vol. 85.

Setiawan et al, "Diagnosis of Coronary Artery Disease Using Artificial Intelligence Based Decision Support System", IEEE, 2009, 5 pages, ICoMMS, Penang, Malaysia.

Zhang, "Wavelet Approach for ECG Baseline Wander Correction and Noise Reduction", IEEE Engineering in Medicine, 2005, 4 pages, Shanghai, China.

\* cited by examiner

ELECTROCARDIOGRAPH (ECG) SIGNAL PROCESSING

TECHNICAL FIELD

Technology described herein relates generally to wearable electronic devices.

BACKGROUND

The popularity of wearable technology, such as smart watches and smart eyewear, has grown in recent years. Wearable technology can include clothing or accessories that incorporate computer and electronic technologies. Wearable technology can perform a variety of functions that are beneficial to a user, in addition to being aesthetically pleasing to the user. For example, wearable technology can provide health monitoring and health metrics, music listening, global positioning system (GPS) capabilities, activity tracking, telephony services, internet browsing, etc. for the user that is wearing the wearable technology.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein.

Figure 1A:
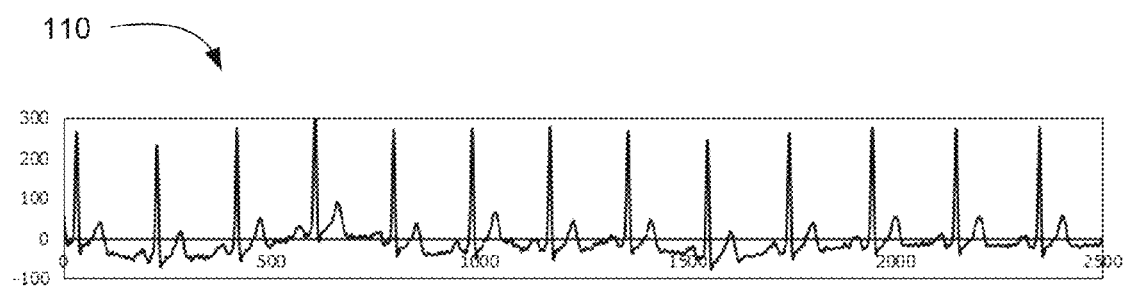
FIG. 1A illustrates an electrocardiograph (ECG) signal with substantially no noise in accordance with an example.

Reference will now be made to the exemplary embodiments illustrated, and specific language will be used herein to describe the same. It will nevertheless be understood that no limitation of the scope of the technology is thereby intended.

DETAILED DESCRIPTION

Before specific invention embodiments are disclosed and described, it is to be understood that this disclosure is not limited to such embodiments, including the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

As used in this specification and the appended claims, the singular forms "a," "an" and "the" include plural referents unless the context clearly dictates otherwise. Thus, for example, reference to "a sensor" includes a plurality of such sensors.

As used herein, the terms "baseline wander," "baseline wander noise," and "noise" can be used interchangeably and refer variation in signal, or to an effect caused by variation in signal, received by an ECG sensor due to causes other than cardiac function. A number of factors may cause or contribute to baseline wander, such as signal interruption or interference, for example, less that optimal or varied (i.e. changing) contact between a subject and a sensor, the presence of bodily fluids (i.e. sweat), or electrical interference from surrounding power sources, such as power lines.

Reference throughout this specification to "an example" means that a particular feature, structure, or characteristic described in connection with the example is included in at least one embodiment of the present invention. Thus, appearances of the phrases "in an example" or "an embodiment" in various places throughout this specification are not necessarily all referring to the same embodiment.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention can be referred to herein along with alternatives for the various components thereof. It is understood that such embodiments, examples, and alternatives are not to be construed as defacto equivalents of one another, but are to be considered as separate and autonomous representations under the present disclosure.

Furthermore, the described features, structures, or characteristics can be combined in any suitable manner in one or more embodiments. In the following description, numerous specific details are provided, such as examples of layouts, distances, network examples, etc., to provide a thorough understanding of invention embodiments. One skilled in the relevant art will recognize, however, that the technology can be practiced without one or more of the specific details, or with other methods, components, layouts, etc. In other instances, well-known structures, materials, or operations are not shown or described in detail to avoid obscuring aspects of the disclosure.

In this specification, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

Example Embodiments

An initial overview of technology embodiments is provided below and then specific technology embodiments are described in further detail later. This initial summary is intended to aid readers in understanding the technology more quickly but is not intended to identify key features or essential features of the technology nor is it intended to limit the scope of the claimed subject matter.

Wearable computing devices include smart watches, health and fitness devices, etc. that enable users to monitor heart rate and physical activity. An electrocardiograph (ECG) is a physiological signal often measured in wearable and mobile computing devices. An ECG is a recording of the electrical activity of a heart measured over time. The ECG can identify electrical impulses generated by polarization and depolarization of cardiac tissue in the heart and translate the electrical impulses into an ECG signal. The ECG signal is then used to measure a rate and regularity of heartbeats, a size and position of heart chambers, a presence of damage to the heart, whether a certain area of the heart is contributing more or less to the electrical activity of the heart than expected, etc. Measurements of the ECG signal can be used for a wide range of applications, such as cardiac monitoring, biometrics for authentication, wellness and fitness, and stress and emotion modeling.

The ECG signal can be measured via a sensor on the wearable device connected to the user. In other words, the user's ECG can be measured using electrodes that are attached to the user's skin. Signal processing techniques can be used to extract parameters of interest from the ECG signal. Various features or characteristics of the ECG signal can be identified and interpreted in order to classify a cardiac state of the user. For example, certain features of the ECG signal can indicate a normal ECG, an abnormal ECG, a presence of arrhythmia, etc.

FIG. 1A illustrates an exemplary electrocardiograph (ECG) signal 110. The ECG signal 110 can represent electrical activity of a user's heart. The ECG signal 110 can be represented as a voltage (in mV) over a period of time (in seconds). The ECG signal 110 can be measured using a wearable device (with a sensor) that is attached to the user's body. The ECG signal 110 can include a plurality of individual waveforms that can be periodic or aperiodic in nature. For example, each individual waveform in the ECG signal 110 can have a starting location and an ending location. In addition, each individual waveform in the ECG signal 110 can include a spike (also known as an R peak). The ECG signal 110 shown in FIG. 1A is not affected by noise (e.g., baseline wander noise).

Figure 1B:
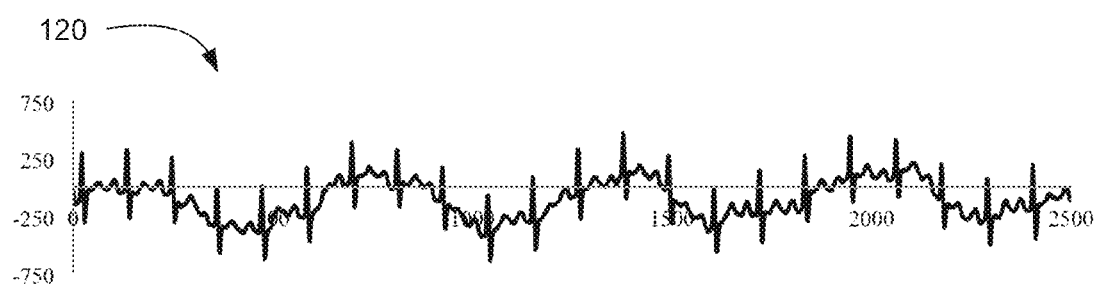
FIG. 1B illustrates a noisy electrocardiograph (ECG) signal in accordance with an example.

FIG. 1B illustrates an exemplary noisy electrocardiograph (ECG) signal 120. For example, the ECG signal 120 can be affected by baseline wander noise. The ECG signal 120 that is affected by baseline wander noise can be sinusoidal in shape. The baseline wander noise can be caused by poor contact between ECG sensors (or electrodes) and the user's skin. In addition, the poor contact can occur because of variation in contact pressure between the skin and the ECG sensor due to patient perspiration or movement of the ECG sensor (e.g., the user can move when the ECG is being measured). The presence of baseline wander noise can result in low-frequency oscillations in the ECG signal 120 and as a result, the individual waves in the ECG signal 120 no longer have the same reference axis. The various features or characteristics of the noisy ECG signal 120 can be unidentifiable because of the distortions in the noisy ECG signal (i.e., the baseline wander noise). As a result, whether the user's ECG is normal, abnormal, etc. can be difficult to determine because the ECG signal is noisy.

Additional problems can result from the baseline wander noise in the ECG signal 120. The intermediate waveforms in the ECG signal 120 can be difficult to detect due to the fluctuating reference axis across the entire ECG signal. Crucial measurements can be contained in these undetected or partially detected intermediate waveforms in the ECG signal 120, thereby potentially causing incorrect interpretation of the user's cardiac state. In one example, automatically extracting information or parameters from the noisy ECG waveform can be increasingly complex since additional signal processing techniques are required to remove the baseline wander noise from the ECG signal 120. When the wearable device is running continuously sensing applications, complex signal processing techniques can disadvantageously impact the wearable device's battery life. This disadvantage can be magnified for applications involving multi-lead or multi-strip ECG measurements. In addition, numerous applications involve real-time response (e.g., physiotherapy exercise monitoring, cardiac monitoring) and using complex techniques to denoise the ECG signal 120 can be impractical.

Figure 2:
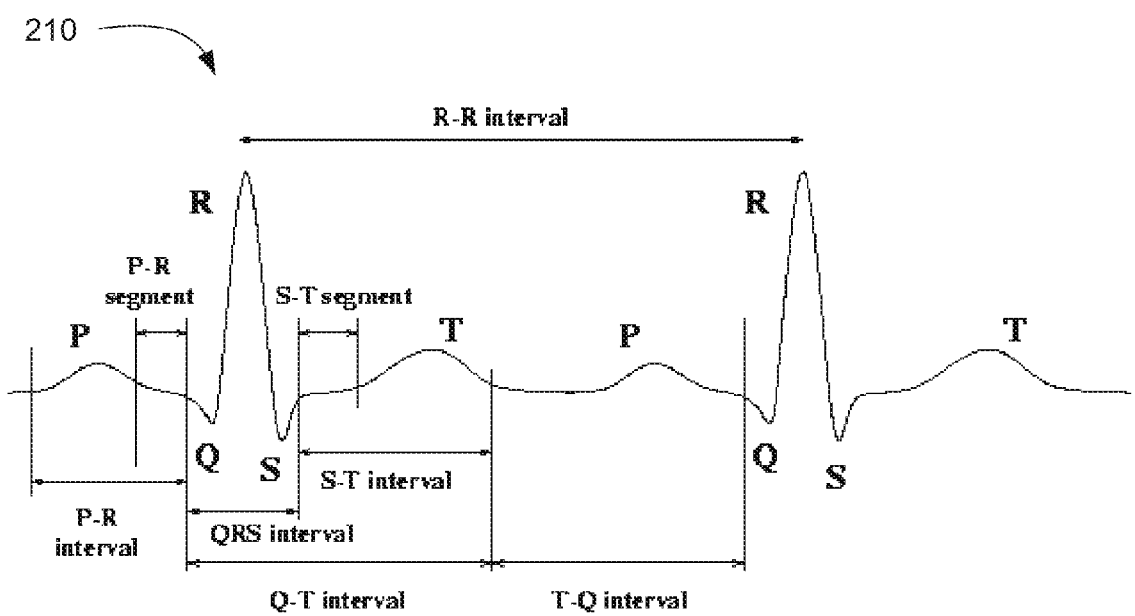
FIG. 2 illustrates various features of an electrocardiograph (ECG) waveform in accordance with an example.

FIG. 2 illustrates various features in an exemplary electrocardiograph (ECG) waveform 210. The ECG signal can be an electrical representation of heart activity over a period of time. The ECG waveform 210 can include a P wave, an R wave, a QRS wave complex, T wave, etc. Time-domain features for interpreting the ECG waveform 210 can include intra-wave parameters (e.g., features within a given ECG waveform) or inter-wave parameters (e.g., features between successive ECG waveforms). Each waveform in the ECG signal can include a start time, an end time, and an R peak. The intra-wave features can include wave amplitudes and time intervals (e.g., PR Interval, QRS Width, QT interval, ST segment etc.) between different sections of the ECG signal. The inter-wave parameters can include a time interval between successive waveforms in the ECG signal. In total, more than 40 time-domain features can be estimated in order to accurately interpret the ECG signal.

The features in the ECG waveform 210 can include, but are not limited to, an RR interval, the PR interval, a PR segment, the QRS wave complex, a J-point, the ST segment, an ST interval, and the QT interval. The RR interval, approximately 0.6 seconds (s) to 1.2 s in duration, can be an interval between an R wave and the next R wave. The PR interval, approximately 120 milliseconds (ms) to 200 ms in duration, can be measured from the beginning of the P wave to the beginning of the QRS wave complex. The PR segment, approximately 50 ms to 120 ms in duration, can connect the P wave and the QRS wave complex. The QRS wave complex, approximately 80 ms to 120 ms in duration, can reflect a rapid depolarization of the right and left ventricles in the heart. The J-point can represent a point at which the QRS wave complex finishes and the ST segment begins. The ST segment, approximately 320 ms in duration, can be measured from the J-point to the end of the T wave. The QT interval can be measured from the beginning of the QRS wave complex to the end of the T wave.

In one example, inferences on the user's cardiac state can be made based on the features of the ECG waveform 210. For example, a shorted QT interval or a prolonged QT interval can indicate hyperkalemia or certain genetic abnormalities. A flattened or inverted T wave can indicate coronary ischemia, hypocalcemia, etc. Hyperacute T waves can indicate acute myocardial infarction. Numerous other inferences about the user's cardiac state can be determined based on the various features of the ECG waveform 210.

As described herein, a novel technique can be performed directly on the noisy ECG signal to extract features without complex processing or error correction. The ECG signal can be processed in two steps: (1) Individual waveforms of a noisy ECG signal (i.e., an ECG signal corrupted or distorted by baseline-wander noise) and their respective locations can be detected without missing any waveforms; and (2) Feature extraction techniques can be directly applied on the original noisy ECG signal once the locations of the individual waveforms are detected. The novel technique described herein can improve prior ECG signal denoising techniques that are complex and challenging to implement in wearable applications. The novel technique described herein can extract information from the noisy ECG signal without adding additional noise or distortion to the ECG signal. In addition, the novel technique described herein can be well-suited for continuous sensing applications that operate on wearable devices.

Figure 3:
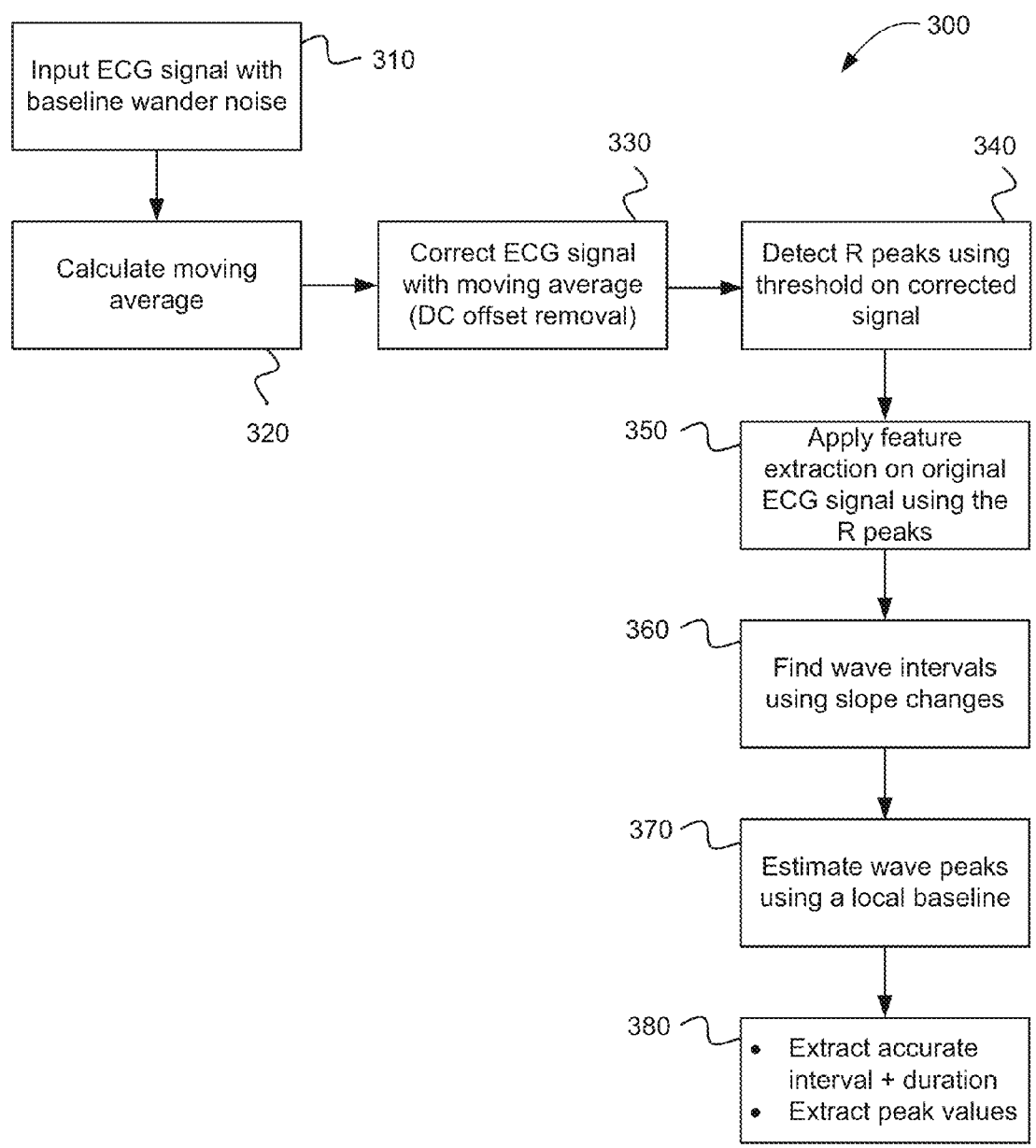
FIG. 3 is a block diagram describing signal processing technique that is performed on a noisy electrocardiograph (ECG) signal in accordance with an example.

FIG. 3 is a block diagram 300 illustrating exemplary signal processing that is performed on a noisy electrocardiograph (ECG) signal. Noisy ECG signals generally have a fluctuating reference axis, and therefore, amplitudes in the noisy ECG signals cannot be accurately measured. Signal processing can be performed on the noisy ECG signal in order to detect individual characteristic waveforms and associated waveform locations in the noisy ECG signal. Features can be extracted for each individual waveform in the noisy ECG signal based on the waveform locations. In other words, the features can be detected on a per wave basis.

In step 310, the noisy ECG signal (e.g., an ECG signal with baseline wander noise) can be identified. The noisy ECG signal can be measured via a sensor on a wearable device. In step 320, a moving average can be calculated from the noisy ECG signal. The moving average for the noisy ECG signal, also known as a running average, can be an average of a set of samples beginning with the first sample. The next element in the moving average can begin from the second sample using the same number of samples, and so on. In other words, calculating the moving average involves creating a series of averages of different subsets of a data set. A first element of the moving average can be obtained by taking an average of an initial fixed subset of the data set. Then the subset can be modified by "shifting forward"; that is, excluding the first number of the data set. A new subset of numbers can be created and the average can be determined for the new subset of numbers. This process can be repeated over the entire data set.

In step 330, the moving average can be removed or subtracted from the noisy ECG signal in order to correct the noisy ECG signal. The moving average can correspond to low frequency baseline drift of the noisy ECG signal. Therefore, removing the moving average from the ECG signal can result in a direct current (DC) offset being removed from each of the individual waveforms in the ECG signal. The removal of the DC offset can result in an ECG signal that is substantially noiseless (as illustrated in FIG. 4B). The noisy ECG signal that has been corrected so that the baseline wander noise has been substantially removed can be referred to as a corrected ECG signal.

In step 340, the most prominent peaks in the corrected ECG signal (e.g., the R peaks) and peak locations for each of the R peaks can be detected. The R peak can be a marker for each individual waveform in the ECG signal. In one configuration, the R peak locations can be detected from the corrected ECG signal using a defined threshold. For example, sections of the ECG signal that have peak values higher than the defined threshold (e.g., 70%) can be identified. A maximum value for each of these sections in the ECG signal can be identified, wherein the maximum value designates the R peak location. Thus, the R peak locations for each of the individual waveforms in the corrected ECG signal can be detected as a function of time. As a non-limiting example, the first R peak location in the corrected ECG signal can be at 0.8 seconds, the second R peak location in the corrected ECG signal can be at 1.65 seconds, and so on.

In step 350, feature extraction can be applied on the original ECG signal (i.e., the ECG signal affected by baseline wander noise) using the R peak locations identified in the corrected ECG signal. In other words, the corrected ECG signal (i.e., the noise-corrected ECG signal) cannot be used for further processing due to distortion in the corrected ECG signal. Rather, the detected R peak locations and the original noisy ECG signal can be used for feature extraction. The known R peak locations in the corrected ECG signal (e.g., the first R peak location at 0.8 seconds, the second R peak location at 1.65 seconds, and so on) can correspond, in time, to the R peak locations in the noisy ECG signal. In other words, in the noisy ECG signal, the first R peak location is also at 0.8 seconds, the second R peak location is also at 1.65 seconds, and so on.

In step 360, ECG features (e.g., inter-wave intra-wave time intervals, amplitudes, amplitude ratios, etc.) can be identified for each individual waveform in the noisy ECG signal. Since the R peak locations are known in the noisy ECG signal, other wave intervals in the noisy ECG signal (e.g., P waves, T waves) can be determined for each individual waveform based on the R peak locations. As previously described, the P wave can occur in the ECG waveform before the R peak, and the T wave can occur in the ECG waveform after the R peak. For each P wave and T wave, an onset and offset value can be determined. The onset value can refer to a beginning of the P wave or the T wave. The offset value can refer to an end of the P wave or the T wave. The onset and offset values can be determined by identifying slope changes in the individual waveform in the noisy ECG signal immediately to the right of the R peak (i.e., for the T wave) and immediately to the left of the R peak (i.e., for the P wave). The slope changes can be positive or negative. In one example, the onset and offset values can be detected based on locations within the individual waveform in the ECG signal that indicate maximum slope changes. In one configuration, slope changes in the individual waveform in the ECG signal can be sought in accordance with known approximate time ranges. For example, Q peaks can occur approximately 200 ms after the P peak, the R peak can occur approximately 800 ms after the Q peak, etc. If a slope change is not detected, that individual waveform in the noisy ECG signal can be classified as being abnormal.

In step 370, wave peaks (e.g., P peaks and T peaks) can be identified for each individual waveform in the noisy ECG signal using a local baseline. In other words, the baseline can be localized for each individual waveform in the noisy ECG signal. In one example, onset or offset values for a wave (e.g., the P wave) included in the individual waveform can be used as a local reference axis. In general, the reference axis for a noisy ECG signal can be improper since, for example, the amplitude of the ECG signal can be moved by an offset value due to the baseline wander noise. Therefore, the amplitude of a wave onset or offset (e.g., P wave onset, T-wave offset), or alternatively, the amplitude of a wave peak (e.g., an amplitude for the P wave peak), can be set as the local reference for that particular waveform in the noisy ECG signal. The amplitudes for the R wave, the T wave, etc. can be measured with respect to the local reference. In other words, when determining the amplitudes of the various waves (and wave peaks) in the individual waveform in the noisy ECG signal, a common reference basis can be used in the individual waveform. Other waveforms in the noisy ECG signal may use a different local reference. Rather than using a unique reference for all the waveforms in the noisy ECG signal, the local reference can be set per each individual waveform. In one example, the local reference for each ECG waveform can be identified using a slope technique (i.e., the onset value for setting the local reference can be determined based on slope changes in the individual waveform).

In step 380, features such as wave intervals and time durations for each of the wave intervals can be determined for each individual waveform in the noisy ECG signal. The wave intervals can be determined with respect to the local reference for each individual waveform in the noisy ECG signal. In addition, peak values can be identified for each individual waveform in the noisy ECG signal with respect to the local reference. For example, peak values for the P peak, T peak, etc. can be determined for each individual waveform in the ECG signal.

Based on the wave intervals and peak values, various features can be extracted from each individual waveform in the noisy ECG signal. For example, PR intervals, R-R intervals, QT segments, etc. can be extracted from the noisy ECG signal. Each of the extracted features can represent cardiac function metrics, such as atrial depolarization, ventricular polarization or depolarization, etc. These physiological phenomena can be directly reflected in the ECG waveform as a combination of wave peaks, wave onsets, wave offsets, wave intervals, etc.

Figure 4A:
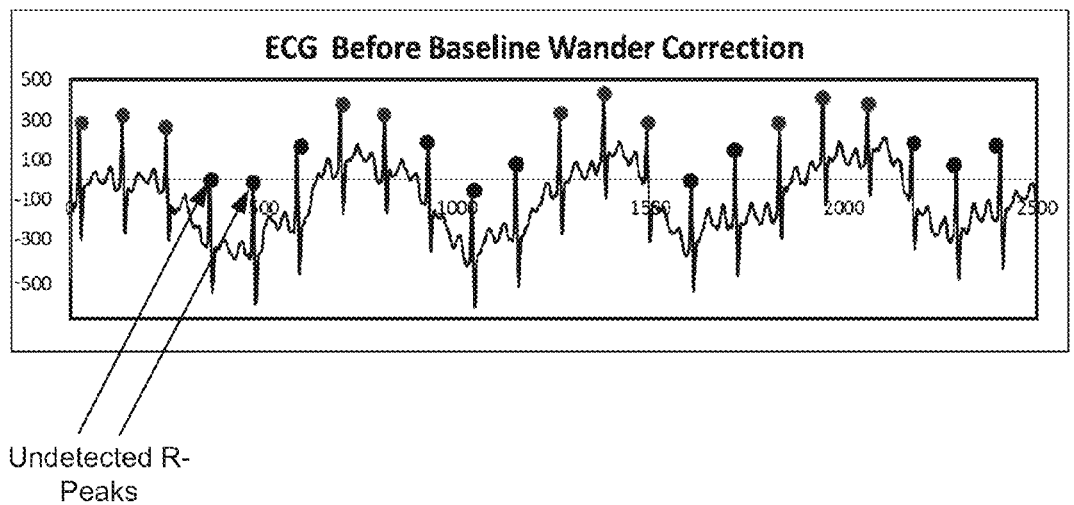
FIG. 4A illustrates an electrocardiograph (ECG) signal without noise correction in accordance with an example.
Figure 4B:
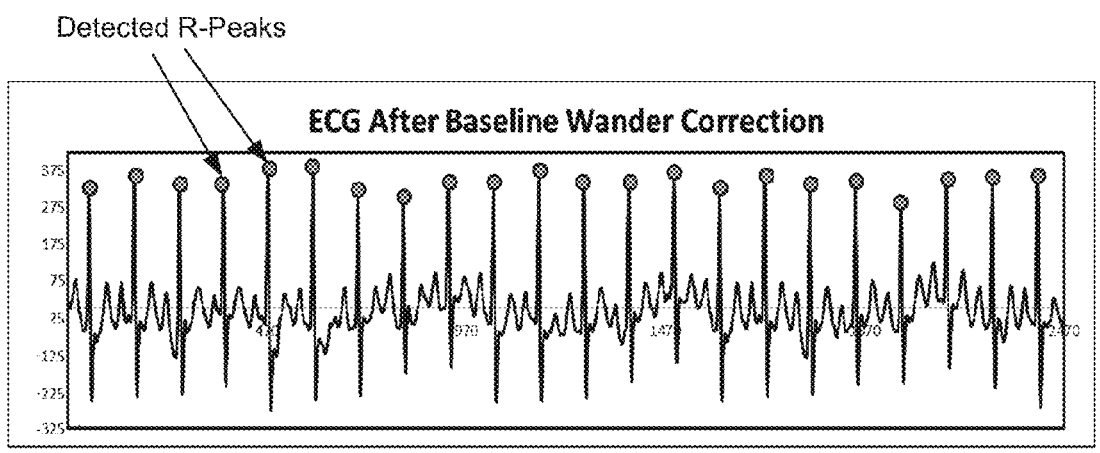
FIG. 4B illustrates an electrocardiograph (ECG) signal after noise correction in accordance with an example.

FIG. 4A illustrates an exemplary electrocardiograph (ECG) signal without noise correction. In other words, the ECG signal can be affected by baseline wander noise. The ECG signal that is affected by baseline wander noise can be sinusoidal in shape. In addition, the noisy ECG signal can include a plurality of undetected signal peaks (e.g., undetected R peaks).

FIG. 4B illustrates an exemplary electrocardiograph (ECG) signal after noise correction. After performing baseline wander correction (i.e., DC offset correction or removal), previously undetected R peaks in the noisy ECG signal can now indicate comparable values to other R peaks in the ECG waveform. In other words, detected R peaks can be revealed in the corrected ECG waveform.

Figure 5:
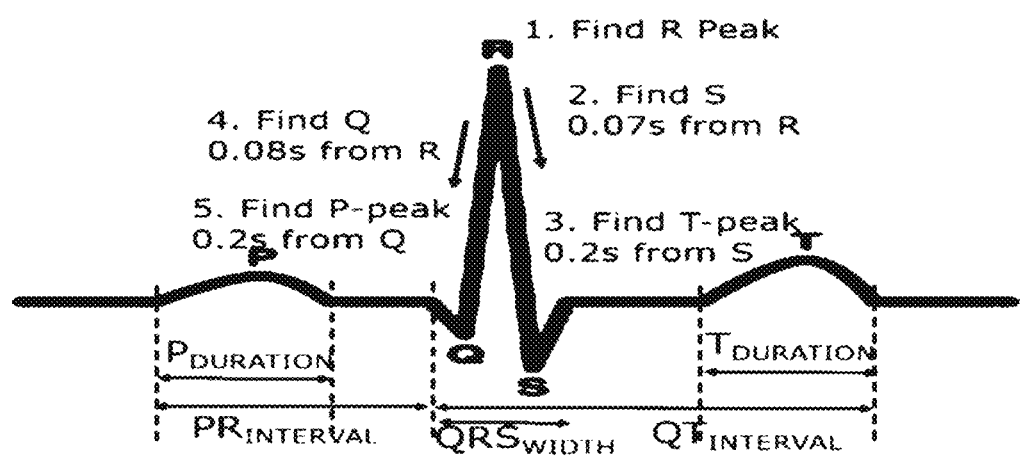
FIG. 5 illustrates various peak locations extracted from an electrocardiograph (ECG) signal waveform in accordance with an example.

FIG. 5 illustrates various features extracted from an electrocardiograph (ECG) waveform. The ECG waveform illustrated in FIG. 5 can be one of a plurality of ECG waveforms in an ECG signal. The ECG waveform can include an R peak, an S peak, a T peak, a Q peak and a P peak. A location of the R peak can be determined upon removing a DC offset from a noisy ECG signal. Slope changes may be used to detect the wave onsets and wave offsets in the ECG waveform. To detect the peak values, local maxima or minima may be identified in specific time ranges beginning from the R peak. For example, slope changes immediately to the right of the R peak can be identified in order to identify the S peak. In particular, a maximum slope change immediately to the right of the R peak can indicate a presence of the S peak. As an example, the S peak can be located as being 0.07 seconds forward in time from the R peak. Similarly, the T peak can be identified to the right of the S peak based on slope changes. As an example, the T peak can be located as being 0.2 seconds forward in time from the S peak. In one example, slope changes immediately to the left of the R peak can be identified in order to identify the Q peak. In particular, a maximum slope change immediately to the left of the R peak can indicate a presence of the Q peak. As an example, the Q peak can be located as being 0.08 seconds earlier in time from the R peak. Similarly, the P peak can be identified to the left of the Q peak based on slope changes. As an example, the P peak can be located as being 0.2 seconds earlier in time from the Q peak.

Figure 6:
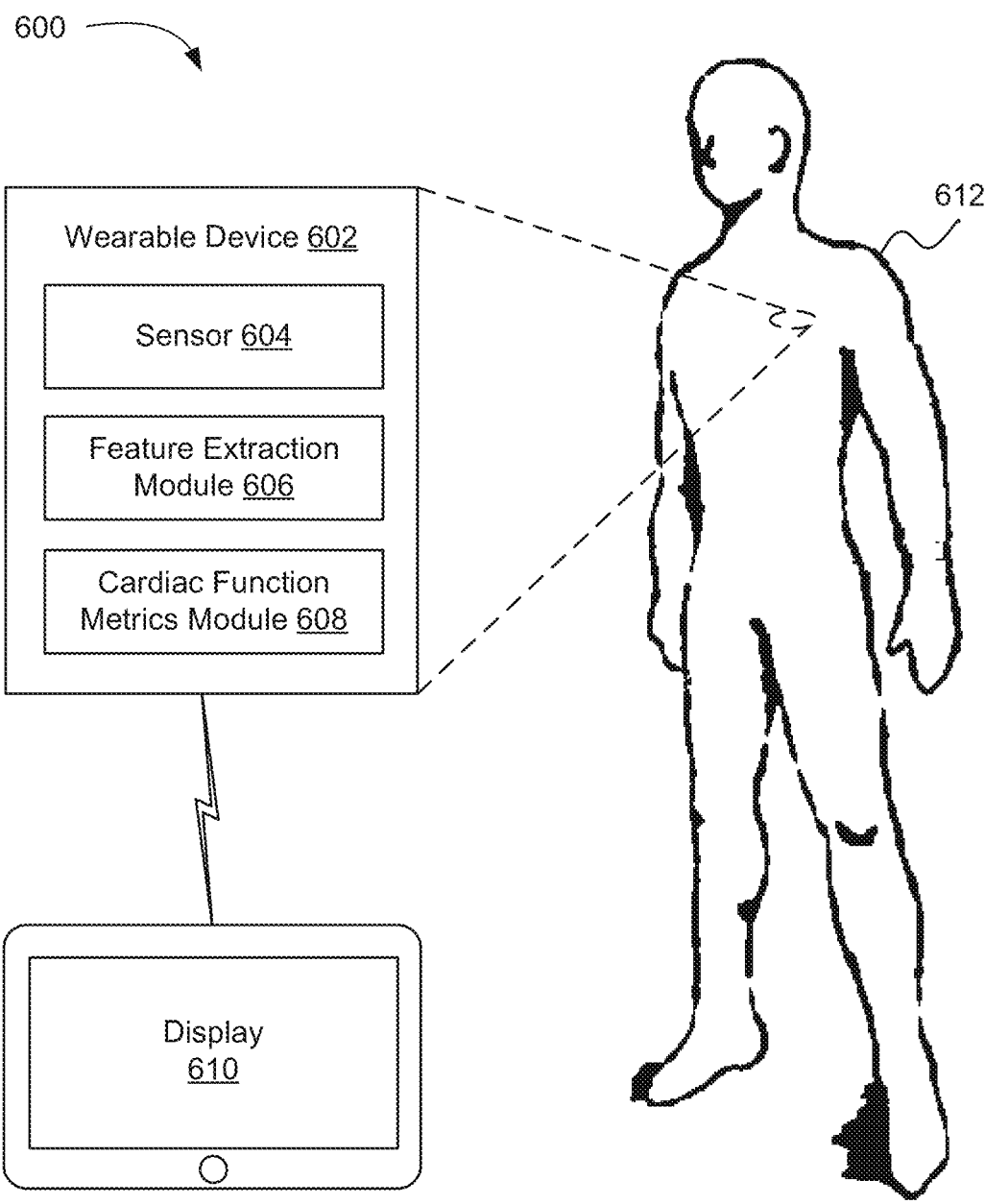
FIG. 6 illustrates a wearable device that is operable to extract features from a noisy electrocardiograph (ECG) signal and determine cardiac function metrics based on the features in accordance with an example.

FIG. 6 illustrates an exemplary system 600 comprising a wearable device 602 operable to extract features from a noisy electrocardiograph (ECG) signal and determine cardiac function metrics based on the features. The wearable device 602 can include a sensor 604, a feature extraction module 606 and a cardiac function metrics module 608. The sensor 604 can be attached to a user 612 via electrodes that are attached to the user's skin. Thus, the wearable device 602 can, via the sensor 604, measure electrical activity of the user's heart over a period of time. In general, various features can be extracted from the measured ECG signal (e.g., amplitude and time intervals for individual waveforms in the ECG signal). The features extracted from the ECG signal can infer whether the user's heart beat is normal, abnormal, etc.

In one configuration, the ECG signal measured at the sensor 604 can be affected by noise, such as baseline wander noise. Therefore, signal processing can be performed on the noisy ECG signal and then the features can be extracted for individual waveforms in the noisy ECG signal. The feature extraction module 606 can calculate a moving average for the noisy ECG signal. The moving average for the noisy ECG signal can be an average of a set of samples beginning with the first sample. The next element in the moving average can begin from the second sample using the same number of samples, and so on. The feature extraction module 606 can remove the moving average from the noisy ECG signal in order to obtain a corrected ECG signal that is substantially noiseless. In other words, a direct current (DC) offset can be removed from the noisy ECG signal, thereby resulting in the corrected ECG signal. The feature extraction module 606 can determine a plurality of R peak locations in the corrected ECG signal using a defined threshold.

The feature extraction module 606 can select an R peak location in an individual waveform in the noisy ECG signal using the plurality of R peak locations that are identified in the corrected ECG signal. In other words, the R peak locations in the corrected ECG signal correspond with the R peak locations in the noisy ECG signal. The feature extraction module 606 can determine an onset value for a P wave in the individual waveform and an offset value for the P wave in the individual waveform. In addition, the feature extraction module 606 can determine an onset value for a T wave in the individual waveform and an offset value for the T wave in the individual waveform. For example, the feature extraction module 606 can identify one or more slope changes in the individual waveform in the noisy ECG signal. These slope changes can occur on the individual waveform either before the R peak in time or after the R peak in time. The locations for the P wave and the T wave (e.g., the onset values and offset values for the P wave and the T wave, respectively) can be identified in the individual waveform in the noisy ECG signal based on the one or more slope changes.

In one configuration, the feature extraction module 606 can select a local reference point in the individual waveform in the noisy ECG signal using an amplitude associated with one of the onset value for the P wave or the onset value for the T wave. The feature extraction module 606 can determine one or more peak amplitudes in the individual waveform in the noisy ECG signal with respect to the local reference point, wherein the peak locations include a P peak location and a T peak location. In other words, the feature extraction module 606 can assign amplitudes for each of the P wave, the R wave, the T wave, etc. with respect to the local reference point. The feature extraction module 606 can extract features from the individual waveform in the noisy ECG signal using the peak locations with respect to the local reference point.

The cardiac function metrics module 608 can infer cardiac function metrics based on the features extracted from the noisy ECG signal. The cardiac function metrics can indicate whether the user's heart is healthy or unhealthy based on the features of the noisy ECG signal. For example, an R-R interval, PR interval, and other features of the noisy ECG signal can indicate various cardiac function metrics, such as an abnormal heart beat or a normal heart beat (i.e., a heartbeat within an acceptable range). Certain cardiac function metrics can indicate whether the user 612 has medical concerns (e.g., hyperkalemia, hypocalcemia) based on the features extracted from the noisy ECG signal. The cardiac function metrics module 608 can notify the user 612 to contact a health care professional when the extracted features from the ECG signal indicate potential abnormalities.

The cardiac function metrics module 608 can provide the cardiac function metrics to a display 610. Therefore, the user 612 can view the cardiac function metrics determined by the wearable device 602. In one example, the display 610 can be included in the wearable device 602. Alternatively, the display 610 can be part of a computing device that is external to the wearable device 602. In another example, the cardiac function metrics module 608 can provide the features extracted from the noisy ECG signal and/or the cardiac function metrics to a cloud back-end computing system for further processing or logging.

The wearable device 602 can use various standards and protocols to transmit data (e.g., cardiac function metrics or other health information related to the user 612) to external computing devices. For example, the wearable device 602 can use orthogonal frequency-division multiple access (OFDMA) in a downlink (DL) transmission and single carrier frequency division multiple access (SC-FDMA) in an uplink (UL) transmission. Standards and protocols that use orthogonal frequency-division multiplexing (OFDM) for signal transmission include the third generation partnership project (3GPP) long term evolution (LTE), (e.g. Releases 8, 9, 10 or 11), the Institute of Electrical and Electronics Engineers (IEEE) 802.16 standard (e.g., 802.16e or 802.16m), which is commonly known to industry groups as WiMAX (Worldwide interoperability for Microwave Access), and the IEEE 802.11 standard (e.g. 802.11-2012, 802.11ac, 802.11ad), which is commonly known to industry groups as WiFi.

The wearable device 602 can be capable of communicating via licensed spectrum, such as through a cellular network, and via unlicensed spectrum, such as via a WiFi hotspot. WiFi is a common name provided to the IEEE 802.11 set of standards for communicating in unlicensed spectrum including the 2.4, 3.7 and 5 GHz frequency bands. The set of standards includes the IEEE 802.11a standard released in 1999 for communication in the 5 GHz and 3.7 GHz band, the IEEE 802.11b standard, also released in 1999 for communication in the 2.4 GHz band, the 802.11g standard released in 2003 for communication in the 2.4 GHz range via orthogonal frequency division multiplexing (OFDM) and/or direct sequence spread spectrum (DSSS), and the 802.11n standard released in 2009 for communication in the 2.4 GHz and 5 GHz bands using multiple-input multiple-output (MIMO). Other examples of communication standards utilized at the wearable device 602 can include Bluetooth, Bluetooth low energy, low power WiFi, or other wireless local area network standards.

Figure 7:
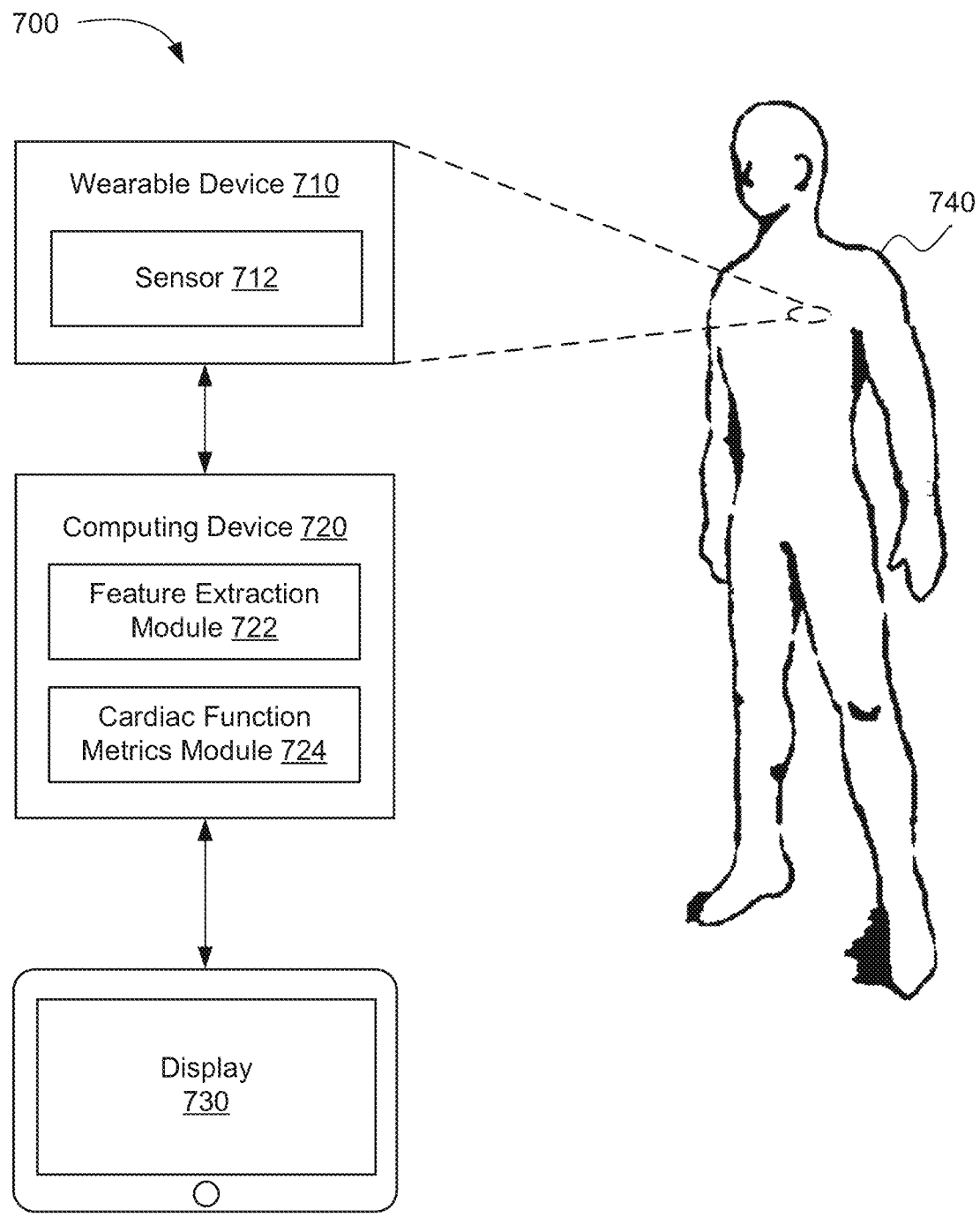
FIG. 7 illustrates a wearable device that is operable to measure an electrocardiograph (ECG) signal and communicate the ECG signal to a computing device for extraction of features from the ECG signal in accordance with an example.

FIG. 7 illustrates an exemplary system 700 comprising a wearable device 710 operable to measure an electrocardiograph (ECG) signal and communicate the ECG signal to a computing device 720 for extraction of features from the ECG signal. The wearable device 710 can be attached to a user 740 via electrodes that are attached to the user's skin. The wearable device 710 can include a sensor 712 for measuring electrical activity of the user's heart over a period of time. The wearable device 710 can communicate the ECG signal to the computing device 720, for example, using WiFi, Bluetooth, etc. In other words, the computing device 720 may be located external to the wearable device 710. The computing device 720 can extract various features from the ECG signal in order to determine whether the user's heart beat is normal, abnormal, etc.

A feature extraction module 722 in the computing device 720 can identify the ECG signal received from the wearable device 710. The feature extraction module 722 can preprocess the ECG signal including both clean and noisy ECG signals in order to detect the individual waveforms and their respective R peaks in the ECG signal. The feature extraction module 722 can subsequently perform additional signal processing on the ECG signal in order to extract features for individual waveforms in the ECG signal. The feature extraction module 722 can calculate a moving average for the noisy ECG signal, and remove the moving average from the noisy ECG signal in order to obtain a corrected ECG signal that is substantially noiseless. The feature extraction module 722 can determine a plurality of peak locations (e.g., R peak locations) in the corrected ECG signal using a defined threshold.

In one configuration, the feature extraction module 722 can select an R peak location in an individual waveform in the noisy ECG signal using the plurality of peak locations that are identified in the corrected ECG signal. The feature extraction module 722 can determine an onset value for a P wave in the individual waveform and an offset value for the P wave in the individual waveform, and determine an onset value for a T wave in the individual waveform and an offset value for the T wave in the individual waveform. The feature extraction module 722 can select a local reference point in the individual waveform in the noisy ECG signal using an amplitude associated with one of the onset value for the P wave or the onset value for the T wave. In one example, the feature extraction module 722 can determine one or more peak locations (e.g., a P peak location and a T peak location) in the individual waveform in the noisy ECG signal with respect to the local reference point. In addition, the feature extraction module 722 can extract features from the individual waveform in the noisy ECG signal using the peak locations with respect to the local reference point. The features extracted from the individual waveform can include PR intervals, R-R intervals, etc.

A cardiac function metrics module 724 in the computing device 720 can determine cardiac function metrics based on the features extracted from the noisy ECG signal. The cardiac function metrics can indicate whether the user's heart is healthy or unhealthy based on the features of the noisy ECG signal. The cardiac function metrics module 724 can provide the cardiac function metrics to a display 730, thereby allowing the user 740 to view whether the ECG signal is normal or abnormal. The display 730 can be included in the computing device 720 or located external to the computing device 720.

Figure 8:
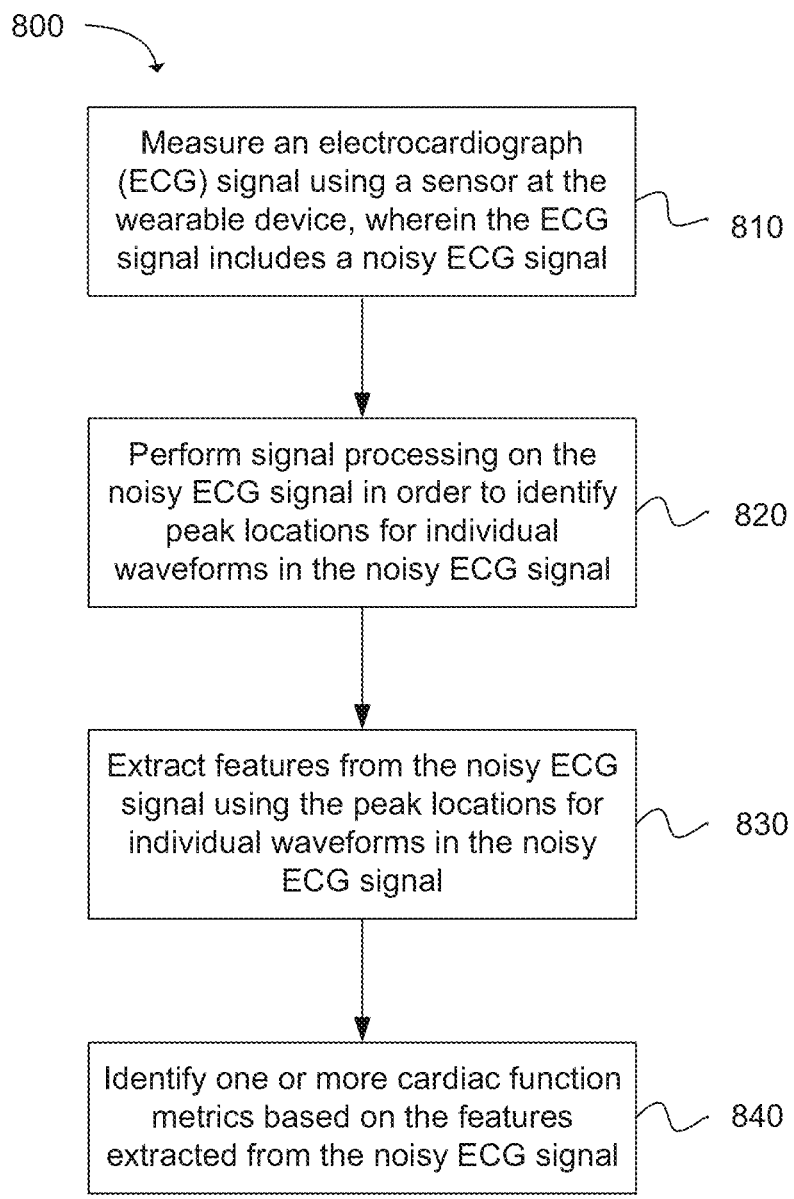
FIG. 8 depicts functionality of circuitry of a wearable device operable to determine cardiac function metrics of a subject in accordance with an example.

Another example provides functionality 800 of circuitry of a wearable device operable to determine cardiac function metrics of a subject, as shown in the flow chart in FIG. 8. The functionality can be implemented as a method or the functionality can be executed as instructions on a machine, where the instructions are included on at least one computer readable medium or one non-transitory machine readable storage medium. The wearable device can be configured to measure an electrocardiograph (ECG) signal using a sensor at the wearable device, wherein the ECG signal includes a noisy ECG signal, as in block 810. The wearable device can be configured to perform signal processing on the noisy ECG signal in order to identify peak locations for individual waveforms in the noisy ECG signal, as in block 820. The wearable device can be configured to extract features from the noisy ECG signal using the peak locations for individual waveforms in the noisy ECG signal, as in block 830. In addition, the wearable device can be configured to identify one or more cardiac function metrics based on the features extracted from the noisy ECG signal, as in block 840.

In one configuration, the wearable device can be further configured to provide the cardiac function metrics for display on the wearable device. In one example, the noisy ECG signal is affected by baseline wander noise. In another example, the one or more cardiac function metrics indicate at least one of a healthy ECG signal for the subject attached to the wearable device or an unhealthy ECG signal for the subject attached to the wearable device.

In one aspect, the features extracted from the individual waveforms in the noisy ECG signal include wave amplitudes and time intervals for the individual waveforms in the noisy ECG signal. In addition, the features extracted from the individual waveforms in the noisy ECG include at least one of: a PR interval, a QRS width, a QT interval, an ST segment, or an R-R interval.

In one configuration, the wearable device can be further configured to: calculate a moving average for the noisy ECG signal; remove the moving average from the noisy ECG signal in order to obtain a corrected ECG signal that is substantially noiseless, wherein removing the moving average from the noisy ECG signal comprises removing a direct current (DC) offset from the noisy ECG signal; and determine a plurality of R peak locations in the corrected ECG signal using a defined threshold. In addition, the wearable device can be further configured to: select an R peak location in an individual waveform in the noisy ECG signal using the plurality of R peak locations that are determined in the corrected ECG signal that is substantially noiseless; identify a P peak location for a P peak and a T peak location for a T peak in the individual waveform in the noisy ECG signal using the R peak location and local maxima on the noisy ECG signal; identify a Q wave location and an S wave location in the individual waveform in the noisy ECG signal using local minima on the noisy ECG signal; determine an onset value for the P peak and an offset value for the P peak using slope changes in the noisy ECG signal; determine an onset value for the T peak and an offset value for the T peak using slope changes in the noisy ECG signal; select a local reference point in the individual waveform in the noisy ECG signal using an amplitude associated with one of: the onset value for the P peak, the offset value for the P peak, the onset value for the T peak, or the offset value for the T peak; and extract features from the individual waveform in the noisy ECG signal with respect to the local reference point, wherein the features are used to identify the cardiac function metrics. In one example, the wearable device can be further configured to: identify one or more slope changes in the individual waveform in the noisy ECG signal; and identify the P peak location and the T peak location in the individual waveform in the noisy ECG signal using the one or more slope changes.

Figure 9:
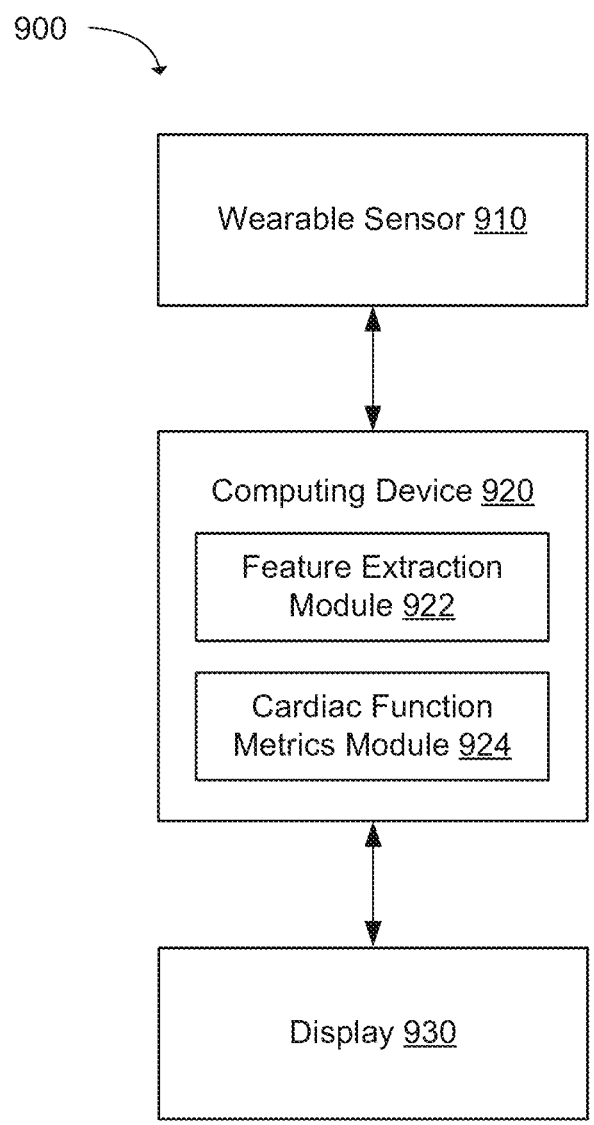
FIG. 9 depicts a system operable to detect cardiac function metrics in a subject using signal features in accordance with an example.

Another example provides functionality 900 of a system operable to detect cardiac function metrics in a subject using signal features, as shown in the flow chart in FIG. 9. The functionality can be implemented as a method or the functionality can be executed as instructions on a machine, where the instructions are included on at least one computer readable medium or one non-transitory machine readable storage medium. The system 900 can include a wearable sensor 910 configured to receive an electrocardiograph (ECG) signal from the subject, wherein the ECG signal includes a noisy ECG signal. The system 900 can include a feature extraction module 922 configured to: perform signal processing on the noisy ECG signal in order to identify peak locations for individual waveforms in the noisy ECG signal, and extract features from the noisy ECG signal using the peak locations for individual waveforms in the noisy ECG signal. The system 900 can include a cardiac function metrics module 924 configured to identify one or more cardiac function metrics based on the features extracted from noisy ECG signal. In one configuration, the feature extraction module 922 and the cardiac function metrics module 924 can be included in a computing device 920 of the system 900. The system 900 can include a display 930 configured to receive the cardiac function metrics from the controller and display the cardiac function metrics to an operator of the system.

In one example, at least one of: the feature extraction module 922, the cardiac function metrics module 924, or the display 930 is located external to the wearable sensor 910. In another example, the noisy ECG signal is affected by baseline wander noise. In an additional example, the features extracted from the individual waveforms in the noisy ECG signal include wave amplitudes and time intervals for the individual waveforms in the noisy ECG signal. In yet another example, the features extracted from the individual waveforms in the noisy ECG include at least one of: a PR interval, a QRS width, a QT interval, an ST segment, or an R-R interval.

In one example, the feature extraction module 922 is further configured to: calculate a moving average for the noisy ECG signal; remove the moving average from the noisy ECG signal in order to obtain a corrected ECG signal that is substantially noiseless, wherein removing the moving average from the noisy ECG signal comprises removing a direct current (DC) offset from the noisy ECG signal; and determine a plurality of R peak locations in the corrected ECG signal using a defined threshold. In addition, the feature extraction module 922 can be further configured to: select an R peak location in an individual waveform in the noisy ECG signal using the plurality of peak locations that are determined in the corrected ECG signal that is substantially noiseless; identify a P peak location for a P peak and a T peak location for a T peak in the individual waveform in the noisy ECG signal using the R peak location and local maxima on the noisy ECG signal; identify a Q wave location and an S wave location in the individual waveform in the noisy ECG signal using local minima on the noisy ECG signal; determine an onset value for the P peak and an offset value for the P peak using slope changes in the noisy ECG signal; determine an onset value for the T peak and an offset value for the T peak using slope changes in the noisy ECG signal; select a local reference point in the individual waveform in the noisy ECG signal using an amplitude associated with one of: the onset value for the P peak, the offset value for the P peak, the onset value for the T peak, or the offset value for the T peak; and extract features from the individual waveform in the noisy ECG signal with respect to the local reference point, wherein the features are used to identify the one or more cardiac function metrics.

Figure 10:
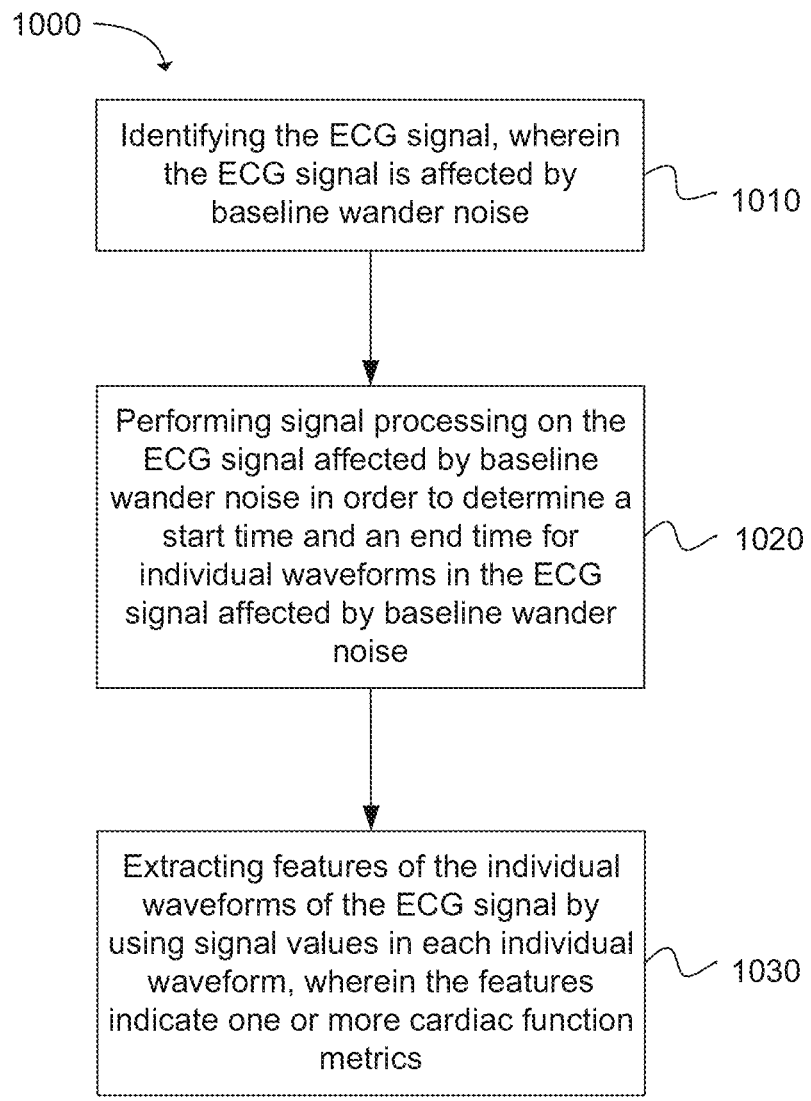
FIG. 10 depicts a flow chart of a method for processing an electrocardiograph (ECG) signal in accordance with an example.

Another example provides a method 1000 for processing an electrocardiograph (ECG) signal, as shown in the flow chart in FIG. 10. The method can be executed as instructions on a machine, where the instructions are included on at least one computer readable medium or one non-transitory machine readable storage medium. The method can include the operation of identifying the ECG signal, wherein the ECG signal is affected by baseline wander noise, as in block 1010. The method can include performing signal processing on the ECG signal affected by baseline wander noise in order to determine a start time and an end time for individual waveforms in the ECG signal affected by baseline wander noise, as in block 1020. In addition, the method can include extracting features of the individual waveforms of the ECG signal by using signal values in each individual waveform, wherein the features indicate one or more cardiac function metrics, as in block 1030.

In one example, the method can include measuring the ECG signal using a sensor in a wearable device that is attached to a user. In another example, the method can include determining the cardiac function metrics to indicate at least one of a healthy ECG signal or an unhealthy ECG signal based on the features extracted in the individual waveforms in the ECG signal.

In one configuration, the step of performing the signal processing on the ECG signal affected by baseline wander further comprises: calculating a moving average for the ECG signal affected by baseline wander noise; removing the moving average from the ECG signal affected by baseline wander noise in order to obtain a corrected ECG signal that is substantially noiseless; and determining a plurality of peak locations in the corrected ECG signal using a defined threshold, the peak locations in the corrected ECG signal identifying locations of a plurality of R peaks. In other words, an R peak location may be determined in an individual waveform in the ECG signal by calculating the moving average of the ECG signal and then subtracting the moving average from the original ECG signal that is affected by baseline wander noise.

In addition, the method further comprises: selecting an R peak location in an individual waveform in the ECG signal affected by baseline wander noise using the plurality of peak locations that are determined in the corrected ECG signal that is substantially noiseless; identifying a P peak location for a P peak and a T peak location for a T peak in the individual waveform in the ECG signal affected by baseline wander noise using the R peak location and local maximum on the noisy ECG signal; identifying a Q wave location and an S wave location in the individual waveform in the noisy ECG signal using local minima on the noisy ECG signal; determining an onset value for the P peak and an offset value for the P peak using slope changes in the noisy ECG signal; determining an onset value for the T peak and an offset value for the T peak using slope changes in the noisy ECG signal; selecting a local reference point in the individual waveform in the ECG signal affected by baseline wander noise using an amplitude associated with one of: the onset value for the P peak, the offset value for the P peak, the onset value for the T peak, or the offset value for the T peak; and extracting features from the individual waveform in the ECG signal affected by baseline wander noise with respect to the local reference point, wherein the features are used to identify the one or more cardiac function metrics. In other words, signal processing may be performed on the ECG signal affected by baseline wander noise beginning from the R-peak to detect the other individual waves in the ECG waveform (e.g., P-wave, T-wave, Q and S waves) by determining local minima and maxima points at different locations of the ECG waveform.

Figure 11:
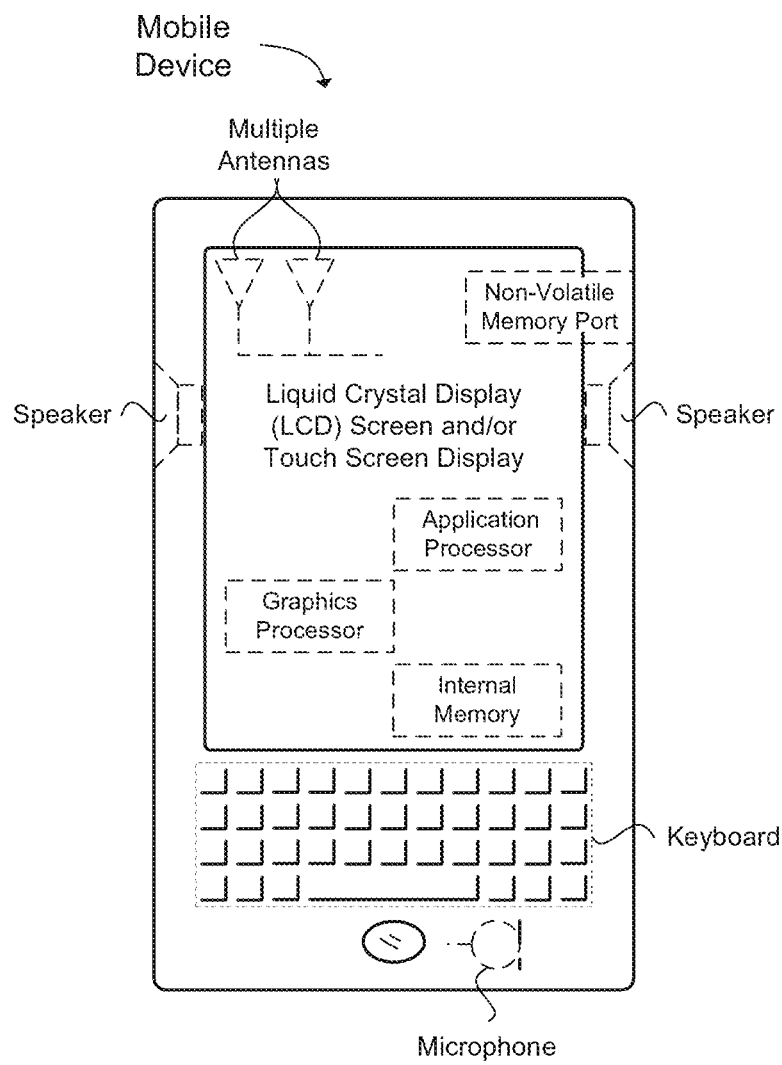
FIG. 11 illustrates a diagram of a wireless device in accordance with an example.

FIG. 11 provides an example illustration of the wireless device, such as a wearable device, a mobile wireless device, a mobile communication device, a tablet, a handset, or other type of wireless device. The wireless device can include one or more antennas configured to communicate with a node, macro node, low power node (LPN), or, transmission station, such as a base station (BS), an evolved Node B (eNB), a baseband unit (BBU), a remote radio head (RRH), a remote radio equipment (RRE), a relay station (RS), a radio equipment (RE), or other type of wireless wide area network (WWAN) access point. The wireless device can be configured to communicate using at least one wireless communication standard including 3GPP LTE, WiMAX, High Speed Packet Access (HSPA), Bluetooth, and WiFi. The wireless device can communicate using separate antennas for each wireless communication standard or shared antennas for multiple wireless communication standards. The wireless device can communicate in a wireless local area network (WLAN), a wireless personal area network (WPAN), and/or a WWAN.

FIG. 11 also provides an illustration of a microphone and one or more speakers that can be used for audio input and output from the wireless device. The display screen can be a liquid crystal display (LCD) screen, or other type of display screen such as an organic light emitting diode (OLED) display. The display screen can be configured as a touch screen. The touch screen can use capacitive, resistive, or another type of touch screen technology. An application processor and a graphics processor can be coupled to internal memory to provide processing and display capabilities. A non-volatile memory port can also be used to provide data input/output options to a user. The non-volatile memory port can also be used to expand the memory capabilities of the wireless device. A keyboard can be integrated with the wireless device or wirelessly connected to the wireless device to provide additional user input. A virtual keyboard can also be provided using the touch screen.

Various techniques, or certain aspects or portions thereof, can take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a RAM, EPROM, flash drive, optical drive, magnetic hard drive, solid state drive, or other medium for storing electronic data. The node and wireless device can also include a transceiver module, a counter module, a processing module, and/or a clock module or timer module. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations.

It should be understood that many of the functional units described in this specification have been labeled as modules, in order to more particularly emphasize their implementation independence. For example, a module can be implemented as a hardware circuit comprising custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like.

Modules can also be implemented in software for execution by various types of processors. An identified module of executable code can, for instance, comprise one or more physical or logical blocks of computer instructions, which can, for instance, be organized as an object, procedure, or function. Nevertheless, the executables of an identified module need not be physically located together, but can comprise disparate instructions stored in different locations which, when joined logically together, comprise the module and achieve the stated purpose for the module.

Indeed, a module of executable code can be a single instruction, or many instructions, and can even be distributed over several different code segments, among different programs, and across several memory devices. Similarly, operational data can be identified and illustrated herein within modules, and can be embodied in any suitable form and organized within any suitable type of data structure. The operational data can be collected as a single data set, or can be distributed over different locations including over different storage devices, and can exist, at least partially, merely as electronic signals on a system or network. The modules can be passive or active, including agents operable to perform desired functions.

Examples

The following examples pertain to further embodiments.

In one embodiment there is provided a wearable device operable to determine cardiac function metrics of a subject, the wearable device comprising circuitry configured to:

measure an electrocardiograph (ECG) signal using a sensor at the wearable device, wherein the ECG signal includes a noisy ECG signal;

perform signal processing on the noisy ECG signal in order to identify peak locations for individual waveforms in the noisy ECG signal;

extract features from the noisy ECG signal using the peak locations for individual waveforms in the noisy ECG signal; and identify one or more cardiac function metrics based on the features extracted from the noisy ECG signal.

In one embodiment, the wearable device can be configured to provide the cardiac function metrics for display on the wearable device.

In one embodiment, the noisy ECG signal is affected by baseline wander noise.

In one embodiment, the one or more cardiac function metrics indicate at least one of a healthy ECG signal for the subject attached to the wearable device or an unhealthy ECG signal for the subject attached to the wearable device.

In one embodiment, the features extracted from the individual waveforms in the noisy ECG signal include wave amplitudes and time intervals for the individual waveforms in the noisy ECG signal.

In one embodiment, the features extracted from the individual waveforms in the noisy ECG include at least one of: a PR interval, a QRS width, a QT interval, an ST segment, or an R-R interval.

In one embodiment, the wearable device can be further configured to:

calculate a moving average for the noisy ECG signal;

remove the moving average from the noisy ECG signal in order to obtain a corrected ECG signal that is substantially noiseless, wherein removing the moving average from the noisy ECG signal comprises removing a direct current (DC) offset from the noisy ECG signal; and determine a plurality of R peak locations in the corrected ECG signal using a defined threshold.

In one embodiment, the wearable device can be further configured to:

select an R peak location in an individual waveform in the noisy ECG signal using the plurality of R peak locations that are determined in the corrected ECG signal that is substantially noiseless;

identify a P peak location for a P peak and a T peak location for a T peak in the individual waveform in the noisy ECG signal using the R peak location and local maxima on the noisy ECG signal;

identify a Q wave location and an S wave location in the individual waveform in the noisy ECG signal using local minima on the noisy ECG signal;

determine an onset value for the P peak and an offset value for the P peak using slope changes in the noisy ECG signal;

determine an onset value for the T peak and an offset value for the T peak using slope changes in the noisy ECG signal;

select a local reference point in the individual waveform in the noisy ECG signal using an amplitude associated with one of: the onset value for the P peak, the offset value for the P peak, the onset value for the T peak, or the offset value for the T peak; and extract features from the individual waveform in the noisy ECG signal with respect to the local reference point, wherein the features are used to identify the cardiac function metrics.

In one embodiment, the wearable device can be further configured to:

identify one or more slope changes in the individual waveform in the noisy ECG signal; and identify the P peak location and the T peak location in the individual waveform in the noisy ECG signal using the one or more slope changes.

In one invention embodiment, there is provided a system operable to detect cardiac function metrics in a subject using signal features, the system comprising:

a wearable sensor configured to receive an electrocardiograph (ECG) signal from the subject, wherein the ECG signal includes a noisy ECG signal;

a feature extraction module configured to:

perform signal processing on the noisy ECG signal in order to identify peak locations for individual waveforms in the noisy ECG signal; and extract features from the noisy ECG signal using the peak locations for individual waveforms in the noisy ECG signal;

a cardiac function metrics module configured to identify one or more cardiac function metrics based on the features extracted from noisy ECG signal; and a display configured to receive the cardiac function metrics and display the cardiac function metrics to an operator of the system.

In one embodiment, at least one of: the feature extraction module, the cardiac function metrics module, or the display is located external to the wearable sensor.

In one embodiment, the noisy ECG signal is affected by baseline wander noise.

In one embodiment, the features extracted from the individual waveforms in the noisy ECG signal include wave amplitudes and time intervals for the individual waveforms in the noisy ECG signal.

In one embodiment, the features extracted from the individual waveforms in the noisy ECG include at least one of: a PR interval, a QRS width, a QT interval, an ST segment, or an R-R interval.

In one embodiment, the feature extraction module is further configured to:

calculate a moving average for the noisy ECG signal;

remove the moving average from the noisy ECG signal in order to obtain a corrected ECG signal that is substantially noiseless, wherein removing the moving average from the noisy ECG signal comprises removing a direct current (DC) offset from the noisy ECG signal; and determine a plurality of R peak locations in the corrected ECG signal using a defined threshold.

In one example, the feature extraction module is further configured to:

select an R peak location in an individual waveform in the noisy ECG signal using the plurality of peak locations that are determined in the corrected ECG signal that is substantially noiseless;

identify a P peak location for a P peak and a T peak location for a T peak in the individual waveform in the noisy ECG signal using the R peak location and local maxima on the noisy ECG signal;

identify a Q wave location and an S wave location in the individual waveform in the noisy ECG signal using local minima on the noisy ECG signal;

determine an onset value for the P peak and an offset value for the P peak using slope changes in the noisy ECG signal;

determine an onset value for the T peak and an offset value for the T peak using slope changes in the noisy ECG signal;

select a local reference point in the individual waveform in the noisy ECG signal using an amplitude associated with one of: the onset value for the P peak, the offset value for the P peak, the onset value for the T peak, or the offset value for the T peak; and extract features from the individual waveform in the noisy ECG signal with respect to the local reference point, wherein the features are used to identify the one or more cardiac function metrics.

In one invention embodiment, there is provided a method for processing an electrocardiograph (ECG) signal, the method comprising:

under control of one or more computer systems configured with executable instructions:

identifying the ECG signal, wherein the ECG signal is affected by baseline wander noise, using a processor;

performing signal processing on the ECG signal affected by baseline wander noise in order to determine a start time and an end time for individual waveforms in the ECG signal affected by baseline wander noise, using the processor; and extracting features of the individual waveforms of the ECG signal by using signal values in each individual waveform, wherein the features indicate one or more cardiac function metrics, using the processor.

In one embodiment, such a method can further comprise measuring the ECG signal using a sensor in a wearable device that is attached to a user.

In one embodiment, such a method can further comprise determining the cardiac function metrics to indicate at least one of a healthy ECG signal or an unhealthy ECG signal based on the features extracted in the individual waveforms in the ECG signal.

In one embodiment, performing the signal processing on the ECG signal affected by baseline wander further comprises:

calculating a moving average for the ECG signal affected by baseline wander noise;

removing the moving average from the ECG signal affected by baseline wander noise in order to obtain a corrected ECG signal that is substantially noiseless; and determining a plurality of peak locations in the corrected ECG signal using a defined threshold, the peak locations in the corrected ECG signal identifying locations of a plurality of R peaks.

In one embodiment, such a method can further comprise:

selecting an R peak location in an individual waveform in the ECG signal affected by baseline wander noise using the plurality of peak locations that are determined in the corrected ECG signal that is substantially noiseless;

identifying a P peak location for a P peak and a T peak location for a T peak in the individual waveform in the ECG signal affected by baseline wander noise using the R peak location and local maxima on the noisy ECG signal;

identifying a Q wave location and an S wave location in the individual waveform in the noisy ECG signal using local minima on the noisy ECG signal;

determining an onset value for the P peak and an offset value for the P peak using slope changes in the noisy ECG signal;

determining an onset value for the T peak and an offset value for the T peak using slope changes in the noisy ECG signal;

selecting a local reference point in the individual waveform in the ECG signal affected by baseline wander noise using an amplitude associated with one of: the onset value for the P peak, the offset value for the P peak, the onset value for the T peak, or the offset value for the T peak; and extracting features from the individual waveform in the ECG signal affected by baseline wander noise with respect to the local reference point, wherein the features are used to identify the one or more cardiac function metrics.

In one embodiment, there is provided at least one non-transitory machine readable storage medium comprising a plurality of instructions adapted to be executed to implement the methods recited herein.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the disclosure. Accordingly, it is not intended that the disclosure be limited, except as by the claims set forth below.

What is claimed is:

1. A wearable device operable to determine cardiac function metrics of a subject, the wearable device comprising circuitry configured to:

measure an electrocardiograph (ECG) signal using a sensor at the wearable device, wherein the ECG signal includes a noisy ECG signal;

remove a moving average of the noisy ECG from the noisy ECG signal in order to obtain a corrected ECG signal;

determine a plurality of R peak locations in the corrected ECG signal;

identify R peak locations for individual waveforms in the noisy ECG signal using the determined plurality of R peak locations in the corrected ECG signal;

extract features from the noisy ECG signal using the R peak locations for individual waveforms in the noisy ECG signal; and identify one or more cardiac function metrics based on the features extracted from the noisy ECG signal.

2. The wearable device of claim 1, further configured to provide the cardiac function metrics for display on the wearable device.

3. The wearable device of claim 1, wherein the noisy ECG signal is affected by baseline wander noise.

4. The wearable device of claim 1, wherein the one or more cardiac function metrics indicate at least one of a healthy ECG signal for the subject attached to the wearable device or an unhealthy ECG signal for the subject attached to the wearable device.

5. The wearable device of claim 1, wherein the features extracted from the individual waveforms in the noisy ECG signal include wave amplitudes and time intervals for the individual waveforms in the noisy ECG signal.

6. The wearable device of claim 1, wherein the features extracted from the individual waveforms in the noisy ECG include at least one of: a PR interval, a QRS width, a QT interval, an ST segment, or an R-R interval.

7. The wearable device of claim 1, wherein the circuitry is further configured to:
calculate the moving average for the noisy ECG signal;
remove the moving average from the noisy ECG signal in order to obtain the corrected ECG signal with noise below a defined threshold, wherein removing the moving average from the noisy ECG signal comprises removing a direct current (DC) offset from the noisy ECG signal; and
determine the plurality of R peak locations in the corrected ECG signal using a defined threshold.

8. The wearable device of claim 7, wherein the circuitry is further configured to:
select an R peak location in an individual waveform in the noisy ECG signal using the plurality of R peak locations that are determined in the corrected ECG signal with noise below the defined threshold;
identify a P peak location for a P peak and a T peak location for a T peak in the individual waveform in the noisy ECG signal using the R peak location and local maxima on the noisy ECG signal;
identify a Q wave location and an S wave location in the individual waveform in the noisy ECG signal using local minima on the noisy ECG signal;
determine an onset value for the P peak and an offset value for the P peak using slope changes in the noisy ECG signal;
determine an onset value for the T peak and an offset value for the T peak using slope changes in the noisy ECG signal;
select a local reference point in the individual waveform in the noisy ECG signal using an amplitude associated with one of: the onset value for the P peak, the offset value for the P peak, the onset value for the T peak, or the offset value for the T peak; and
extract features from the individual waveform in the noisy ECG signal with respect to the local reference point, wherein the features are used to identify the cardiac function metrics.

9. The wearable device of claim 8, wherein the circuitry is further configured to:
identify one or more slope changes in the individual waveform in the noisy ECG signal; and
identify the P peak location and the T peak location in the individual waveform in the noisy ECG signal using the one or more slope changes.

10. A system operable to detect cardiac function metrics in a subject using signal features, the system comprising:
a wearable sensor configured to receive an electrocardiograph (ECG) signal from the subject, wherein the ECG signal includes a noisy ECG signal;
a feature extraction module configured to:
remove a moving average of the noisy ECG from the noisy ECG signal in order to obtain a corrected ECG signal;
determine a plurality of R peak locations in the corrected ECG signal;
identify R peak locations for individual waveforms in the noisy ECG signal using the determined plurality of R peak locations in the corrected ECG signal; and
extract features from the noisy ECG signal using the R peak locations for individual waveforms in the noisy ECG signal;

a cardiac function metrics module configured to identify one or more cardiac function metrics based on the features extracted from noisy ECG signal; and
a display configured to receive the cardiac function metrics and display the cardiac function metrics.

11. The system of claim 10, wherein at least one of: the feature extraction module, the cardiac function metrics module, or the display is located external to the wearable sensor.

12. The system of claim 10, wherein the noisy ECG signal is affected by baseline wander noise.

13. The system of claim 10, wherein the features extracted from the individual waveforms in the noisy ECG signal include wave amplitudes and time intervals for the individual waveforms in the noisy ECG signal.

14. The system of claim 10, wherein the features extracted from the individual waveforms in the noisy ECG include at least one of: a PR interval, a QRS width, a QT interval, an ST segment, or an R-R interval.

15. The system of claim 10, wherein the feature extraction module is further configured to:
calculate the moving average for the noisy ECG signal;
remove the moving average from the noisy ECG signal in order to obtain the corrected ECG signal with noise below a defined threshold, wherein removing the moving average from the noisy ECG signal comprises removing a direct current (DC) offset from the noisy ECG signal; and
determine the plurality of R peak locations in the corrected ECG signal using a defined threshold.

16. The system of claim 15, wherein the feature extraction module is further configured to:
select an R peak location in an individual waveform in the noisy ECG signal using the plurality of R peak locations that are determined in the corrected ECG signal with noise below the defined threshold;
identify a P peak location for a P peak and a T peak location for a T peak in the individual waveform in the noisy ECG signal using the R peak location and local maxima on the noisy ECG signal;
identify a Q wave location and an S wave location in the individual waveform in the noisy ECG signal using local minima on the noisy ECG signal;
determine an onset value for the P peak and an offset value for the P peak using slope changes in the noisy ECG signal;
determine an onset value for the T peak and an offset value for the T peak using slope changes in the noisy ECG signal;
select a local reference point in the individual waveform in the noisy ECG signal using an amplitude associated with one of: the onset value for the P peak, the offset value for the P peak, the onset value for the T peak, or the offset value for the T peak; and
extract features from the individual waveform in the noisy ECG signal with respect to the local reference point, wherein the features are used to identify the one or more cardiac function metrics.

17. A method for processing an electrocardiograph (ECG) signal, using one or more computer systems configured with executable instructions, the method comprising:
identifying the ECG signal, wherein the ECG signal is affected by baseline wander noise, using a processor;
removing a moving average from the ECG signal affected by the baseline wander noise in order to obtain a corrected ECG signal, using the processor;
determining a plurality of R peak locations in the corrected ECG signal, using the processor; and selecting an R peak location in an individual waveform in the ECG signal affected by baseline wander noise using the plurality of R peak locations in the corrected ECG signal, using the processor.

18. The method of claim 17, further comprising measuring the ECG signal using a sensor in a wearable device that is attached to a user.

19. The method of claim 17, further comprising determining a cardiac function metrics to indicate at least one of a healthy ECG signal or an unhealthy ECG signal based on features extracted in the individual waveforms in the ECG signal.

20. The method of claim 17, wherein performing the signal processing on the ECG signal affected by baseline wander further comprises:
    calculating the moving average for the ECG signal affected by baseline wander noise;
    removing the moving average from the ECG signal affected by baseline wander noise in order to obtain the corrected ECG signal with noise below a defined threshold; and
    determining the plurality of R peak locations in the corrected ECG signal using a defined threshold.

21. The method of claim 20, further comprising:
    identifying a P peak location for a P peak and a T peak location for a T peak in the individual waveform in the ECG signal affected by baseline wander noise using the R peak location and local maxima on the noisy ECG signal;
    identifying a Q wave location and an S wave location in the individual waveform in the noisy ECG signal using local minima on the noisy ECG signal;
    determining an onset value for the P peak and an offset value for the P peak using slope changes in the noisy ECG signal;
    determining an onset value for the T peak and an offset value for the T peak using slope changes in the noisy ECG signal;
    selecting a local reference point in the individual waveform in the ECG signal affected by baseline wander noise using an amplitude associated with one of: the onset value for the P peak, the offset value for the P peak, the onset value for the T peak, or the offset value for the T peak; and
    extracting features from the individual waveform in the ECG signal affected by baseline wander noise with respect to the local reference point, wherein the features are used to identify the one or more cardiac function metrics.

22. At least one non-transitory machine readable storage medium comprising a plurality of instructions adapted to be executed to implement the method of claim 17.

* * * * *